(12) United States Patent
Krehel

(10) Patent No.: US 8,172,121 B2
(45) Date of Patent: May 8, 2012

(54) STAPLER POWERED AUXILIARY DEVICE

(75) Inventor: Gregg C. Krehel, Newtown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 12/958,707

(22) Filed: Dec. 2, 2010

(65) Prior Publication Data

US 2011/0068144 A1 Mar. 24, 2011

Related U.S. Application Data

(63) Continuation of application No. 12/195,476, filed on Aug. 21, 2008, now Pat. No. 7,866,524.

(60) Provisional application No. 60/995,004, filed on Sep. 24, 2007.

(51) Int. Cl.
*A61B 17/068* (2006.01)

(52) U.S. Cl. ....... 227/175.1; 227/19; 227/14; 227/176.1

(58) Field of Classification Search ............... 227/175.1, 227/176.1, 14, 19; 222/386, 101
See application file for complete search history.

(56) References Cited

U.S. PATENT DOCUMENTS

| | | | |
|---|---|---|---|
| 4,267,836 A | 5/1981 | Whitney et al. | |
| 4,566,620 A | 1/1986 | Green et al. | |
| 4,608,981 A | 9/1986 | Rothfuss et al. | |
| 4,731,058 A | 3/1988 | Doan | |
| 5,125,296 A * | 6/1992 | Nelson et al. | 81/9.3 |
| 5,547,117 A | 8/1996 | Hamblin et al. | |
| 5,658,300 A | 8/1997 | Bito et al. | |
| 5,702,409 A | 12/1997 | Rayburn et al. | |
| 6,119,913 A | 9/2000 | Adams et al. | |
| 6,248,093 B1 | 6/2001 | Moberg | |
| 6,323,461 B2 | 11/2001 | Flot | |
| 6,325,810 B1 | 12/2001 | Hamilton et al. | |
| 6,681,979 B2 | 1/2004 | Whitman | |
| 6,718,607 B1 * | 4/2004 | Gillet et al. | 29/229 |
| 7,025,226 B2 | 4/2006 | Ramey | |
| 7,077,856 B2 | 7/2006 | Whitman | |
| 7,097,650 B2 | 8/2006 | Weller et al. | |
| 7,563,267 B2 | 7/2009 | Goldfarb et al. | |
| 2005/0033278 A1 | 2/2005 | McClurken et al. | |
| 2005/0145671 A1 | 7/2005 | Viola | |
| 2005/0187576 A1 | 8/2005 | Whitman et al. | |
| 2005/0230453 A1 | 10/2005 | Viola | |
| 2006/0000869 A1 | 1/2006 | Fontayne | |
| 2006/0047305 A1 | 3/2006 | Ortiz et al. | |
| 2006/0047306 A1 | 3/2006 | Ortiz et al. | |
| 2006/0047307 A1 | 3/2006 | Ortiz et al. | |
| 2006/0047308 A1 | 3/2006 | Ortiz et al. | |
| 2006/0085033 A1 | 4/2006 | Criscuolo et al. | |
| 2006/0111738 A1 | 5/2006 | Wenchell | |

(Continued)

FOREIGN PATENT DOCUMENTS

EP 1 782 739 A 5/2007

*Primary Examiner* — Brian D Nash

(57) ABSTRACT

There is disclosed an auxiliary device for injecting material between the jaws of a surgical stapler. The auxiliary device includes a nozzle assembly having a discharge port and a compression assembly having at least one compression roller for forcing material out of the discharge port. The disclosed compression rollers may be formed of an incompressible or compressible material. The auxiliary device also includes a drive mechanism for moving the compression assembly within a nozzle body of the nozzle assembly. There is also disclosed a rupturable capsule for retaining material to be dispensed.

20 Claims, 3 Drawing Sheets

U.S. PATENT DOCUMENTS

| | | |
|---|---|---|
| 2007/0175954 A1 | 8/2007 | Viola |
| 2008/0262390 A1* | 10/2008 | Bangera et al. ............... 600/587 |
| 2009/0069821 A1 | 3/2009 | Farritor et al. |
| 2009/0078737 A1* | 3/2009 | Krehel ....................... 227/176.1 |
| 2009/0695821 | 3/2009 | Farritor et al. |
| 2009/0206142 A1 | 8/2009 | Huitema et al. |

* cited by examiner

STAPLER POWERED AUXILIARY DEVICE

CROSS-REFERENCE TO RELATED APPLICATION

The present application is a continuation of U.S. application Ser. No. 12/195,476 filed Aug. 21, 2008, now U.S. Pat. No. 7,866,524, which claims the benefit of and priority to U.S. Provisional Application Ser. No. 60/995,004 filed Sep. 24, 2007, the entire content of which being incorporated herein by reference.

BACKGROUND

1. Technical field

The present disclosure relates to auxiliary devices for use with surgical staplers. More particularly, the present disclosure relates to a powered materials dispenser designed to compress a capsule of materials and to inject the materials between the jaws of the surgical stapler.

2. Background of Related Art

During certain medical procedures it is often advantageous to add or supply various materials to the tissues being operated on. For example, during stapling of tissue, it may be desirable to place healing or sealing materials, such as anti-microbial materials or hemostatic materials, between the tissues being stapled to facilitate healing, etc. In some surgeries, methods of assisting in joining and/or strengthening the tissues being stapled may be desired. Adhesives may be applied to the tissues and buttress materials may be used to strengthen the tissue connections. The buttress materials are mounted on the jaws of the stapling instrument and stapled to the tissues to reinforce the staple lines and prevent tearing of the stapled tissue. It is often desirable to apply adhesives and/or sealants in conjunction with the buttress materials to better reinforce the staple lines in the tissues and assist in sealing the staple holes.

It is preferable to add these materials to the tissues being stapled at the time of the stapling of the tissues. This typically requires an additional device or materials dispenser, for example, a syringe, to be positioned within the area being operated on, in addition to the stapling apparatus being used, thereby requiring more operating space. In addition, the use of an additional, independent materials dispenser requires an additional set of hands to manipulate and operate it while at the same time reducing visibility of the operating area to the surgeons involved.

Therefore, it would be desirable to provide an auxiliary device in the form of a materials dispenser for integral use with a surgical stapler device. It would further be desirable to provide a powered materials dispenser for use with a surgical stapler device and operable concurrently with the surgical stapler.

SUMMARY

There is disclosed an auxiliary materials dispenser for use in a surgical stapler device which generally includes a nozzle assembly including a nozzle body defining a cavity and having a discharge port. A compression assembly is movably mounted within the cavity of the nozzle body and has a compression roller. The compression assembly is movable between a proximal position wherein the compression roller is spaced from the discharge port to a distal position wherein the compression roller is substantially adjacent the discharge port. A drive mechanism is included and is operable to move the compression assembly between the proximal and distal positions such that the compression roller of the compression assembly urges material contained within the cavity toward the discharge port as the compression assembly moves between the proximal and distal positions.

The compression assembly includes a drive block engagable with the drive mechanism. A clevis arm, having first and second ends, is pivotally mounted to the drive block at the first end. A spindle is mounted to the clevis arm at the second end and the compression roller is mounted on the spindle. In one embodiment, a spring is attached to the clevis arm such that the spring biases the compression roller into engagement with an inner surface of the nozzle body.

The nozzle body includes upper and lower inner surfaces which are spaced further apart at their respective proximal ends and closer together at their respective distal ends such that the upper and lower inner surfaces taper towards the discharge port. The compression roller engages the upper inner surface as it moves between the proximal and distal positions.

The nozzle assembly includes a drive nut affixed within the nozzle body and defining a threaded bore. The drive mechanism includes a drive screw rotatably mounted within the threaded bore of the drive nut. A distal end of the screw is engagable with the compression assemble to move the compression assembly within the nozzle body as the drive screw is rotated within the drive nut. The drive mechanism further includes a motor engagable with the drive screw to rotate the drive screw within the drive nut.

In one embodiment, the drive screw is mounted on a distal end of a cable and a proximal end of the cable is affixed to the motor.

In a particular embodiment, the compression roller is formed of an incompressible material. In an alternative embodiment, the compression roller is formed of a compressible material.

In one embodiment the material to be dispensed is contained within a capsule positioned within the cavity of the nozzle body such that the compression roller compresses the capsule to break the capsule as the compression roller moves between the proximal and distal positions. In a specific embodiment, the capsule has a wall thickness which is greater at the proximal end than at the distal end to create a weakened region at the distal end adjacent the discharge port.

There is further disclosed a surgical stapler device including a handle having a first jaw containing a staple containing cartridge and a second jaw movable relative to the first jaw and having an anvil surface. A nozzle assembly is mounted on one of the first and jaws. The nozzle assembly includes a nozzle body defining a cavity and having a discharge port open to a face of one of the first and second jaws. A compression assembly is movably mounted within the cavity of the nozzle body and includes a compression roller. The compression roller is movable between a proximal position spaced from the discharge port to a distal position substantially adjacent the discharge port. A drive mechanism is also provided and is operable to move the compression roller between the proximal and distal positions such that the compression roller urges material contained within the cavity toward the discharge port as the compression roller moves between the proximal and distal positions.

DESCRIPTION OF THE DRAWINGS

Various embodiments of the presently disclosed materials dispenser for use with a surgical stapling device are disclosed herein with reference to the drawings, wherein.

DETAILED DESCRIPTION OF EMBODIMENTS

Embodiments of the presently disclosed auxiliary materials dispenser will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component further away from the user.

Figure 1:
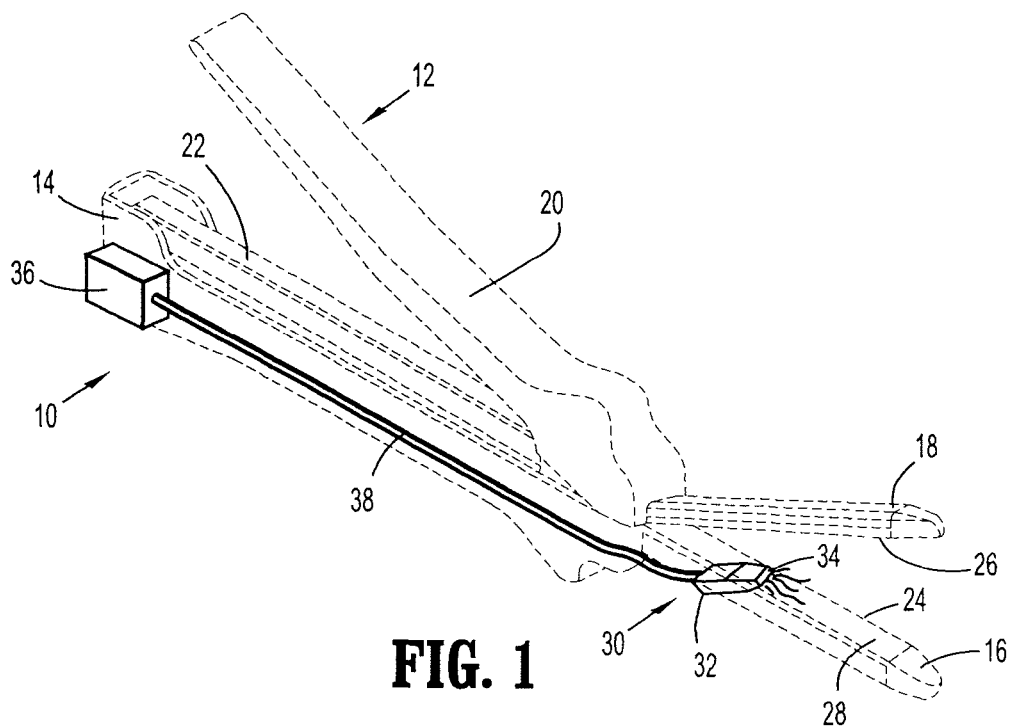
FIG. 1 is a perspective view of one embodiment of a materials dispenser installed in a surgical stapler device.

Referring to FIG. 1, there is disclosed one embodiment of an auxiliary device in the form of a materials dispenser 10 for use in a surgical stapler 12. Materials dispenser 10 may be assembled integral to the associated surgical stapler 12 or may be provided separately and affixed to the desired surgical stapler 12 prior to surgery. Additionally, materials dispenser 10 is configured for use with various types of surgical staplers, such as, for example, endoscopic or open surgery surgical staplers, as well as linear and circular surgical staplers of the open or endoscopic variety.

In the present disclosure, surgical stapler 12 is of the open surgery type including a handle 14 having a fixed lower jaw 16 extending distally from handle 14. A movable upper jaw 18 is movable mounted to handle 14 and is movable from an open position spaced apart from lower jaw 16 to a closed position substantially adjacent lower jaw 16. A trigger 20 is mounted on handle 14 and is operable to move upper jaw 18 between the open and closed positions relative to lower jaw 16. Surgical stapling device 12 further includes an actuation mechanism 22, positioned in handle 14, which is operable with trigger 20 to eject staples (not shown) out of a staple containing cartridge 24, positioned in lower jaw 16, and into an anvil face 26 in upper jaw 18. The tissue to be stapled is captured between anvil face 26 on upper jaw 16 and a cartridge face 28 on staple containing cartridge 24 positioned in lower jaw 16.

Materials dispenser 10 is provided to inject media or material into the tissue receiving space between lower and upper jaws 16 and 18, respectively, to as to apply material "M" to tissue captured therebetween. As use herein, the term "material M" refers to any treatment or other material applied to tissues, or associated support structure, during surgery, such as, for example, antimicrobial, anticoagulant, hemostatic, adhesive, dye or indicating materials, etc. and may take the form of liquids, foams, atomized spray. Materials dispenser 10 generally includes a nozzle assembly 30 having a nozzle body 32 for receipt of material M and a discharge port 34 for passage of material M out of nozzle assembly 30. As shown, nozzle assembly 30 is affixed to, or inserted within one of lower and upper jaws 16 and 18 such that discharge port 34 is open to the space defined between lower and upper jaws 16 and 18, respectively. In the present embodiment, discharge port 34 is provided on lower jaw 16 and extends through staple containing cartridge 24. Discharge port 34 is generally rectangular and is oriented substantially perpendicular to a long axis of staple containing cartridge 24 so as to spray material M across cartridge face 28.

Materials dispenser 10 additionally includes a power source or motor 36 to operate nozzle assembly 30. Motor 36 is provided on handle 14 of surgical stapler 12. Motor 36 is a small DC motor powered by primary or secondary batteries. Various switches (not shown) may be provided on surgical stapler 12 to actuate motor 36. Alternatively, the actuation switch may be provided remotely from surgical stapler 12, such as, a foot switch, etc. A drive cable 38 extends between motor 36 and nozzle assembly 30 and allows motor 36 to be provided remotely from nozzle assembly 30 either on handle 14 of surgical stapler 12 as described herein or remotely off of surgical stapler 12 in order to lighten the weight of surgical stapler 12 for ease of use.

Figure 2:
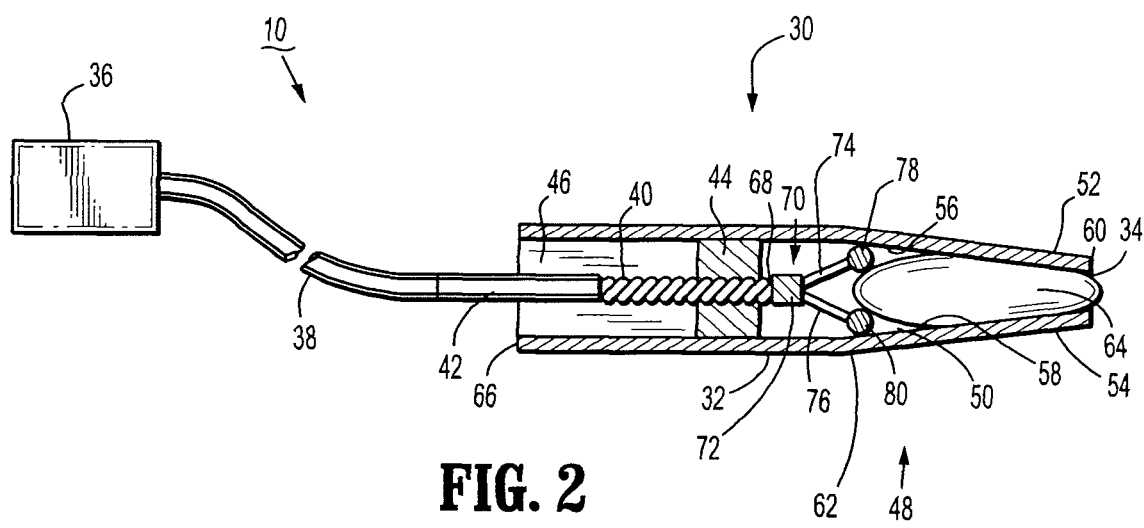
FIG. 2 is a side view, partially shown in section, of the materials dispenser.

Referring to FIG. 2, a threaded drive screw 40 is provided at a distal end 42 of drive cable 38. Threaded drive screw 40 engages a threaded nut 44 positioned within a proximal section 46 of nozzle body 32 such that as drive cable 38 is rotated by drive motor 36, threaded drive screw 40 is rotated within threaded nut 44 to move threaded drive screw 40 within nozzle body 32. Threaded nut 44 can be integral with nozzle body 32 or can be fixed therein by conventional methods such as, for example, welding, gluing, etc.

Nozzle body 32 also includes a tapered distal section 48 extending distally from proximal section 46 and defining a distal space or cavity 50. Tapered distal section 48 includes an upper wall 52 and a lower wall 54 which have upper and lower inner surfaces 56 and 58, respectively. While not specifically shown in FIG. 2, it is obvious that nozzle also includes side wall extending between upper and lower walls 52 and 54 (See FIG. 1). Upper and lower walls 52 and 54 taper distally towards each other to define discharge port 34 at a distal end 60 of distal tapered section 48. The spacing of upper and lower walls 52 and 54 is greatest at a point 62 at the junction of proximal and distal sections 46 and 48, respectively, and closest at discharge port 34 to facilitate squeezing or forcing a source, such as capsule 64, of mater M towards and out of discharge port 34.

A distal end 68 of threaded drive screw 40 is configured to engage and move a compression assembly 70 within tapered distal section 48. Compression assembly 70 is provided to compress and force material M contained within capsule 64 toward and out of discharge port 34. Compression assembly 70 generally includes a drive block 72, engageable with distal end 60 of threaded drive screw, and a pair of upper and lower arms 74 and 76, respectively, extending distally from drive block 72. First and second compression rollers 78 and 80 are mounted on upper and lower arms 74 and 76, respectively. In a specific embodiment, the lengths of first and second compression rollers 78 and 80 are substantially equal to the length of capsule 64 to allow for complete evacuation of capsule 64. First and second compression rollers 78 and 80 are relatively inelastic and may be formed from various materials, such as, for example, hard plastics, stainless steel, ceramic, etc. First and second compression rollers 78 and 80 engage upper and lower inner surfaces 56 and 58 and are moved from a greatest spacing adjacent point 62 of tapered distal section 48 to a closest spacing adjacent discharge port 34 as described herein below.

Figure 3:
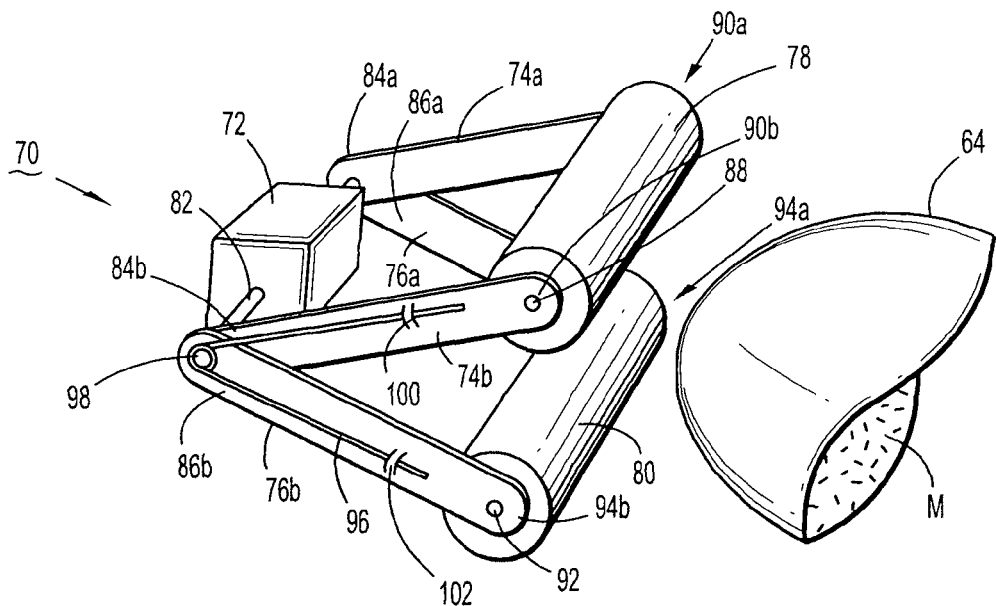
FIG. 3 is a perspective view of the compressing mechanism of the materials dispenser.

Specifically, with reference to FIG. 3, upper arm 74 comprises a pair of upper arms 74*a* and 74*b* supporting first compression roller 78 and lower arm 76 comprises a pair of lower arms 76*a* and 76*b* supporting second compression roller 80. A shaft 82 extends through drive block 72 to rotatably support upper arms 74*a* and 74*b* at proximal ends 84*a* and 84*b* and lower arms 76*a* and 76*b* at proximal ends 86*a* and 86*b*. An upper spindle 88 extends between distal ends 90*a* and 90*b* of upper arms 74*a* and 74*b* and rotatably supports first compression roller 78. First compression roller may be rotatable about upper spindle 88 or affixed to upper spindle 88 such that upper spindle is mounted for rotation within distal ends 90*a* and 90*b*. Similarly, a lower spindle 92 is mounted between distal ends 94*a* and 94*b* of lower arms 76*a* and 76*b* for rotatable support of second compression roller 80.

In order to bias first and second compression rollers 78 and 80 into engagement with upper and lower inner surfaces 56 and 58, respectively, (FIG. 2), compression assembly 70 is provided with a spring 96 having a center point 98 mounted on shaft 82 and connected to upper arm 74*b* at an upper point 100 and lower arm 76*b* at a lower point 102.

Referring now to FIGS. 1-6, and initially with respect to FIG. 1, in use, material dispenser 10 is mounted on surgical stapling device 12 such that discharge port 34 extends through fixed lower jaw 16. Trigger 12 is actuated to cause movable upper jaw 18 to move adjacent fixed lower jaw 16. Continued movement of trigger 12 causes staples (not shown) to be ejected from staple cartridge 24 and toward anvil face 26. In this embodiment, actuation of trigger 12 also operates to activate drive motor 36 thereby rotating drive cable 38. As noted above, other switches or triggering mechanisms, such as foot pedals, etc. may be provided to actuate drive motor 36.

As best shown in FIG. 2, distal end 42 of drive cable 38 engages drive block 72 to move compression assembly 70 distally within distal section 48 of nozzle body 32. Distal movement of compression assembly 70 causes first and second arms 74 and 76 to move distally causing first and second compression rollers 78 and 80 to ride along tapered upper and lower inner surfaces 56 and 58, respectively. As noted above, first and second arms pivot about shaft 82 and spring 96 biases first and second compression rollers 78 and 80 into engagement with upper and lower inner surfaces 56 and 58, respectively, (FIG. 3).

Figure 4:
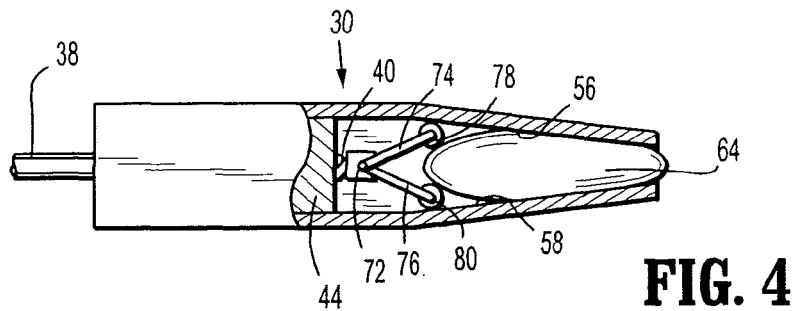
FIG. 4 is a side view, partially shown in section, of a nozzle assembly of the materials dispenser.
Figure 5:
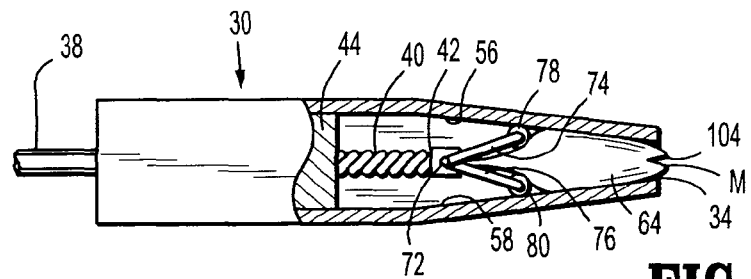
FIG. 5 is a side view, partially shown in section, of the nozzle assembly of the materials dispenser during initial compression of a materials capsule.

Referring now to FIGS. 4 and 5, as first and second compression rollers 78 and 80 move distally from the initial position shown in FIG. 4 to an intermediary position shown in FIG. 5, first and second compression roller engage and compress capsule 64 causing capsule 64 to break at its distal end 104 and spray or otherwise eject material M into the space between fixed lower jaw 16 and movable upper jaw 18 as shown in FIG. 1.

Figure 6:
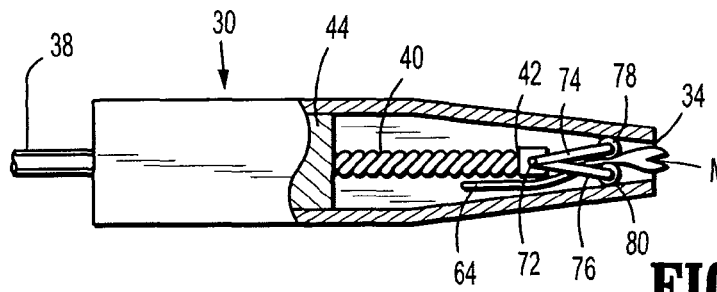
FIG. 6 is a side view, partially shown in section, of the nozzle assembly of the materials dispenser during final compression of the materials capsule.

Finally, with regard to FIG. 6, as first and second compression rollers 78 and 80 move to the distal most and closest positions adjacent discharge port 34, capsule 64 is substantially completely compressed between first and second compression rollers and substantially discharged of material M through discharge port 34.

Figure 7:
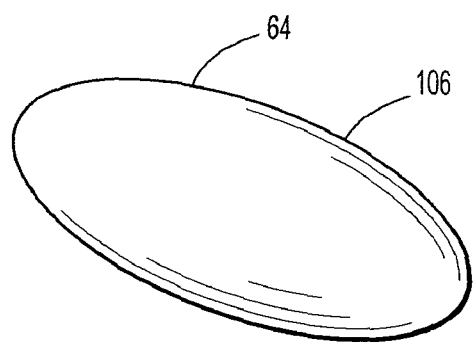
FIG. 7 is a perspective view of one embodiment a materials capsule for use in the materials dispenser.
Figure 8:
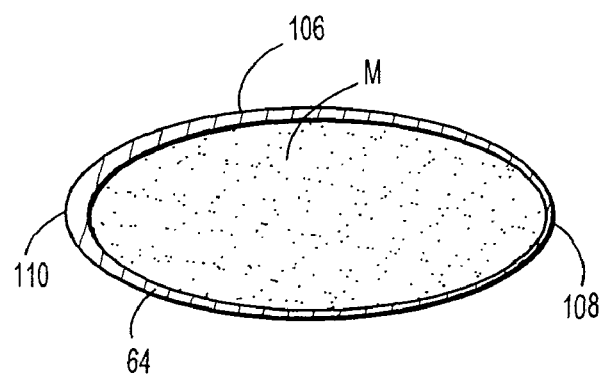
FIG. 8 is a side view, shown in section, of the materials capsule of FIG. 7.

Referring now to FIGS. 7 and 8, and as noted above, capsule 64 is formed from compressible and breakable or rupturable material and is provided to contain material M prior to use. Capsule 64 has a wall 106 configured to contain material M. As best shown in FIG. 7, in a specific embodiment wall 106 is formed with a smaller thickness at a distal end 108 and a larger thickness at a proximal end 110 such that, upon compression, wall 106 will break or burst at the distal end 108 which is position adjacent discharge port 34 of nozzle body 32.

Figure 9:
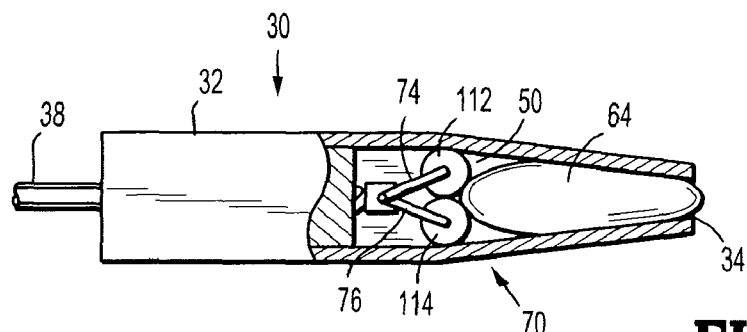
FIG. 9 is a side view, partially shown in section, of an alternate embodiment of a nozzle assembly of a materials dispenser.
Figure 10:
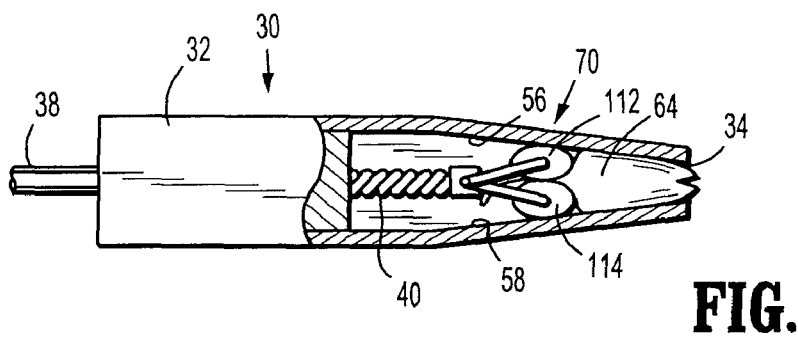
FIG. 10 is a side view, partially shown in section, of the nozzle assembly of FIG. 9 during initial compression of a materials capsule.
Figure 11:
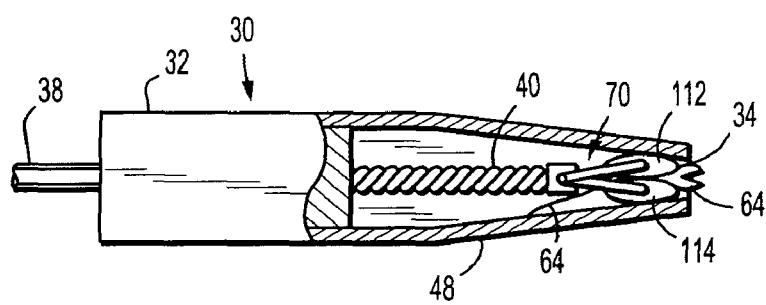
FIG. 11 is a side view, partially shown in section, of the nozzle assembly of FIG. 9 during final compression of the materials capsule.

Referring now to FIGS. 9-11, there are disclosed alternative first and second compression rollers 112 and 114 for use in compression assembly 70. Specifically, first and second compression rollers are formed of a compressible material, such as, for example, foam, soft rubber, etc. First and second compression rollers form a part of compression assembly 70 and are rotatably mounted on upper and lower arms 74 and 76, respectively, substantially as described herein above with regard to first and second compression rollers 78 and 80.

As best shown in FIG. 9, in the initial position, first and second compression rollers 112 and 114 are substantially circular in cross-section and touch to completely enclose cavity 50 and thus capsule 64 contained therein. This allows materials dispenser to be used with capsule 64 or with a lose material not contained within capsule 64.

Referring to FIG. 10, upon actuation materials dispenser 10, first and second compression rollers 112 and 114 move distally along upper and lower inner surfaces 56 and 58, respectively to compress capsule 64, or other material contained within cavity 50, toward discharge port 34. As first and second compression rollers 112 and 114 move distally and against each other, they conform to the decreasing space available between upper and lower inner surfaces 56 and 58 and assume an oval shape or configuration.

Upon complete distal movement of compression assembly 70 within tapered distal section 48 of nozzle body 32, capsule 64 is completely compressed to dispense material M contained therein through discharge port 34. First and second compression rollers 112 and 114 are compressed within the confines of cavity 50 to assume even more oval shapes. In this manner the use of compressible first and second compression rollers 112 and 114 allow first and second compression rollers 112 and 114 to completely seal cavity 50 from the proximal section 46 (FIG. 2) of nozzle body 32 allowing the use of materials M not provided in capsule 64 or otherwise contained.

It will be understood that various modifications may be made to the embodiments disclosed herein. For example, the disclose compression assembly may need only contain a single compression roller. Further, the disclosed materials dispenser may utilize other methods of moving the compression assembly distally within the nozzle assembly, such as, for example, linear moving cables, pneumatics, etc. Additionally, while the disclosed discharge nozzle of the nozzle assembly has been illustrated as being oriented perpendicular to the long axis of the staple containing cartridge, it may alternatively be oriented parallel to the long axis of the staple containing cartridge and discharge material into a knife slot associated with the staple containing cartridge. Therefore, the above description should not be construed as limiting, but merely as exemplifications of particular embodiments. Those skilled in the art will envision other modifications within the scope and spirit of the claims appended hereto.

The invention claimed is:
1. A medicament dispenser for use in a surgical stapler comprising:

a nozzle body defining a longitudinal axis and an opening for passage of medicament disposed in the nozzle body;
a compression assembly including an arm member and a roller rotatably supported on the arm member; and
an actuation assembly including:
an actuation cable;
a lead screw translatably disposed within the nozzle body, the lead screw having a distal end coupled with the arm member of the compression assembly and a proximal end connected with the actuation cable for concomitant rotation with the actuation cable; and
a support member rotatably supporting the lead screw, wherein rotation of the actuation cable causes translation of the lead screw along the longitudinal axis, which in turn moves the roller between proximal and distal positions.

2. The medicament dispenser according to claim 1, wherein the nozzle body is longitudinally tapered toward the opening.

3. The medicament dispenser according to claim 2, wherein the opening is defined in a distal portion of the nozzle body.

4. The medicament dispenser according to claim 3, wherein the medicament is disposed adjacent the opening, such that a distal translation of the lead screw causes the roller to discharge the medicament through the opening.

5. The medicament dispenser according to claim 1, wherein the medicament is contained in a capsule.

6. The medicament dispenser according to claim 5, wherein the capsule has a greater wall thickness at a proximal portion thereof than at a distal portion thereof, whereby a distal translation of the lead screw causes the roller to compress the capsule to break a distal end thereof and discharge the medicament therein through the opening.

7. The medicament dispenser according to claim 1, wherein the roller is made of an inelastic material.

8. The medicament dispenser according to claim 1, wherein the roller is made of a compressible material.

9. The medicament dispenser according to claim 1, further comprising a biasing member configured to urge the roller to move along an inner surface of the nozzle body.

10. A surgical stapler comprising:
a handle;
a first jaw securely fixed to the handle;
a second jaw moveable from an open position spaced apart from the first jaw to a closed position substantially adjacent the first jaw; and
a nozzle assembly including:
a nozzle body defining a longitudinal axis and an opening for passage of medicament disposed in the nozzle body;
a compression assembly including an arm member and a roller rotatably supported on the arm member; and
an actuation assembly including:
an actuation cable;
a lead screw translatably disposed within the nozzle body, the lead screw having a distal end coupled with the arm member of the compression assembly and a proximal end connected with the actuation cable for concomitant rotation with the actuation cable; and
a support member rotatably supporting the lead screw, wherein rotation of the actuation cable causes translation of the lead screw along the longitudinal axis, wherein the nozzle assembly is disposed in one of the first and second jaws, such that the opening is exposed to a space defined between the first and second jaws.

11. The surgical stapler according to claim 10, wherein the nozzle body is longitudinally tapered toward the opening.

12. The surgical stapler according to claim 10, wherein the opening is defined in a distal portion of the nozzle body.

13. The surgical stapler according to claim 12, wherein the medicament is disposed adjacent the opening, such that a distal translation of the lead screw causes the roller to discharge the medicament through the opening.

14. The surgical stapler according to claim 10, wherein the medicament is contained in a capsule.

15. The surgical stapler according to claim 14, wherein the capsule has a greater wall thickness at a proximal portion thereof than at a distal portion thereof, whereby a distal translation of the lead screw causes the roller to compress the capsule to break at its distal end and to discharge the medicament therein through the opening.

16. An end effector for use in surgical stapler comprising:
a jaw assembly including a first jaw and a second jaw;
a nozzle assembly mounted on one of the first and second jaws, the nozzle assembly including a nozzle body defining a cavity and a discharge port;
a compression assembly moveably mounted within the cavity of the nozzle body and having a compression roller, the compression roller being moveable between a proximal position spaced from the discharge port to a distal position substantially adjacent the discharge port; and
a, lead screw rotatably and translatably supported within the cavity of the nozzle assembly, the lead screw coupled with the compression roller, whereby rotation of the lead screw causes translation of the compression roller, wherein the compression roller urges material contained within the cavity toward the discharge port as the compression roller moves between the proximal and distal positions.

17. The end effector for use in surgical stapler according to claim 16, wherein the opening is defined in a distal portion of the nozzle body.

18. The end effector for use in surgical stapler according to claim 16, wherein the roller is made of a compressible material.

19. The end effector for use in surgical stapler according to claim 16, further comprising a biasing member configured to urge the roller to move along an inner surface of the nozzle body.

20. The end effector for use in surgical stapler according to claim 16, wherein
the material is in a capsule disposed in the cavity of the nozzle body.

* * * * *